United States Patent [19]

Terman

[11] Patent Number: 5,091,091
[45] Date of Patent: Feb. 25, 1992

[54] PROTEIN A PERFUSION AND POST PERFUSION DRUG INFUSION

[76] Inventor: David S. Terman, 1200 Moursund Ave., Texas Medical Center, Houston, Tex. 77030

[21] Appl. No.: 563,940

[22] Filed: Aug. 6, 1990

Related U.S. Application Data

[63] Continuation of Ser. No. 331,095, Mar. 27, 1989, abandoned, which is a continuation of Ser. No. 173,227, Mar. 24, 1988, abandoned, which is a continuation of Ser. No. 914,682, Oct. 2, 1986, abandoned, which is a continuation of Ser. No. 540,990, Oct. 2, 1983, abandoned, which is a continuation of Ser. No. 323,326, Nov. 6, 1981, abandoned, which is a continuation of Ser. No. 183,665, Sep. 2, 1980, abandoned.

[51] Int. Cl.$^5$ .............................................. B01D 69/02
[52] U.S. Cl. .................................... 210/632; 210/638; 210/653; 210/266; 210/500.29
[58] Field of Search ............... 210/632, 638, 782, 653, 210/266, 282, 651, 652, 502.1, 500.29; 604/4, 5, 6

[56] References Cited

U.S. PATENT DOCUMENTS 4,243,532  1/1981  Tsuda et al. ...................... 210/196

OTHER PUBLICATIONS

Bansal et al., "Ex Vivo Removal of Serum IgG in a Patient with Colon Carcinoma, Some Biochemical, Immunological and Histological Observations", Cancer, 42, 7/1978.

Primary Examiner—Frank Spear
Attorney, Agent, or Firm—Limbach, Limbach & Sutton

[57] ABSTRACT

Disclosed is extracorporeal plasma perfusion over a therapeutic immobilized protein A (staphylococcal), SPA. The perfused plasma is returned to the host or can be taken off one person and used to treat another and stored in perfused plasma banks. Immobilized protein A quantities, volumes of plasma perfused and the rate of administration based on clinical and toxicity evaluations are set forth. A non-toxic drug infusion during the immediate postperfusion period obtains an observed tumoricidal response far exceeding those due to the extracorporeal plasma perfusion or drug infusion alone representing an in vivo synergism between the perfused plasma and the drug. Also disclosed are the therapeutic protein A cartridge, its loading and delivery system, and a miniaturized immunoabsorbent apparatus enabling the processing of serum samples for testing small quantities of plasma.

52 Claims, 3 Drawing Sheets

PROTEIN A PERFUSION AND POST PERFUSION DRUG INFUSION

CROSS REFERENCE TO RELATED APPLICATION

This is a continuation of co-pending application Ser. No. 07/331,095 filed on Mar. 27, 1989, now abandoned, which is a continuation of application Ser. No. 07/173,227, filed on Mar. 24, 1988, now abandoned, which is a continuation of application Ser. No. 06/914,682, filed on Oct. 2, 1986, now abandoned, which is a continuation of Ser. No. 06/540,990, filed on Oct. 2, 1983, now abandoned which is a continuation of Ser. No. 06/323,326, filed on Nov. 6, 1981, now abandoned, which is a continuation of Ser. No. 06/183,665, filed on Sept. 2, 1980, now abandoned.

BACKGROUND OF THE INVENTION

Immobilized Reagents For Removal Of Circulating Immune Reactants In Vivo

The role of immune reactants in many experimental and human diseases is now well established, Cochrane C. C., Koffler D.: Immune complex disease in experimental animals and man. *Advances Immunol* 16:185-233, 1973; Wilson C. B., Border W. A., Lenham D. H.: Renal diseases in Basic and Clinical Immunology. (Fudenberg, HH, ed.). Lange Publications, Los Altos, Calif., 1976, pg. 562. Therapy for many of these immunologically mediated diseases has consisted largely of the use of pharmacological agents that widely and non-specifically suppress host immunity leading to numerous undesirable effects. With increasing awareness of the etiopathogenic factors in many autoimmune diseases many sensitive radioimmunological techniques to measure them in serum. Various immunoadsorbents designed to extract pathogenic immune reactants from the circulation have been developed. For example, immunoadsorbents consisting of immobilized antigens, antibodies and enzymes have been developed. When placed in an extracorporeal circuit, these immunoadsorbents have shown a capacity to extract or hydrolyze immune reactants in the circulation without demonstrable release of immobilized substances or significant immediate or long-range toxicity to the host.

Graf et al, Graff M. W., Uhr J. W.: Regulation of antibody formation by serum antibody. I. Removal of specific antibody by means of immunoadsorption. *J Exp Med* 50:130-1175, 1969, were the first to show that immunoadsorbents could be employed to selectively remove antibodies from actively and passively immunized rabbits. In later studies, Schenkein et al., Schenkein I., Brystryn J. C., Uhr, J. W.: Specific removal of in vivo antibody by extracorporeal circulation over an immunoadsorbent in gel. *J Clin Invest* 50:1864-1870, 1971, developed an extracorporeal immunoadsorbent system in which bovine serum albumin (BSA) was immobilized in agarose and proved capable of selectively removing BSA antibodies from the circulation. A similar immunoadsorbent in which ssDNA antigen was immobilized and proved capable of extracting ssDNA antibody in both passively and actively immunized rabbits, Terman D. S., Stewart I., Robinette J., Carr R., Harbeck R.: Specific removal of DNA antibodies in vivo with an extracorporeal immunoadsorbent. *Clinical and Experimental Immunology* 24:231-238, 1976. Because of the fragility of the supporting matrix and the possibility of leaching of immobilized substances, new and more stable extracorporeal immunoadsorbents were subsequently developed.

Various antigens such as bovine serum albumin (BSA), deoxyribonucleic acid (DNA), glomerular basement membrane (GBM) extract have been immobilized on several solid supports and these have been employed as extracorporeal immunoadsorbents, Terman D. S., Durante D., Buffaloe G., McIntosh R.: Attenuation of canine nephrotoxic glomerulonephritis with an extracorporeal immunoadsorbent. *Scandinavian Journal of Immunology* 6, 1977: Terman D. S., Petty D., Ogden D., Harbeck R., Buffaloe G., Carr R.: Specific removal of DNA antibodies in vivo by extracorporeal circulation over DNA immobilized in collodion-charcoal. *Clinical Immunology and Immunopathology* 8, 1977; Terman D. S., Tavel T., Petty D., Racic M. R., Buffaloe G.: Specific removal of antibody by extracorporeal circulation over antigen immobilized in collodion-charcoal. *Clinical and Experimental Immunology* 28, 1977; Terman D. S., Tavel T., Petty D., Tavel A., Harbeck R., Buffaloe G., Carr R.: Specific removal of bovine serum albumin (BSA) antibodies by extracorporeal circulation over BSA immobilized in nylon microcapsules. Terman et al, *Journal of Immunology* 116:1337, 1976; Terman D. S., Stewart I., Robinett J., Carr R., Harbeck, R.: Specific removal of DNA antibodies in vivo with an extracorporeal immunoadsorbent. Terman et al, *Clin Exp Immunol* 24:231, 1976.

Circulating immune complexes have now been implicated in the pathogenesis of numerous diseases. Their presence in the circulation often correlates with disease activity and they may be found deposited in tissues, Zubler R. H., Lambert P. H.: Detection of immune complexes in human diseases. *Prog Allergy* 24:1, 1978. In addition to studies described above for hydrolysis of nDNA:antiDNA complexes, preliminary work has shown that Clq, the first component of complement, may be immobilized in collodion membranes and will bind to immune complexes circulated over them. Terman et al *FEBS*, Letters, 68, 89, 1976.

Extracorporeal Approaches To Cancer Therapy

Protein A is a substance which is a constituent of the cell wall of *staphylococcus aureus* Cowan 1 (SPA). It has the capacity to bind the immunoglobulin G (IgG) from most mammalian species and to bind immune complexes. In my studies, I have discovered that when plasma from tumor bearing hosts is perfused over heat killed, formalin fixed SPA which is immobilized in an extracorporeal filtration system, a profound necrotizing tumor killing reaction is observed. Terman et al, *Journal Immunology*, 8, 80, 1980. I have discovered guidelines for use of protein A for patients of various body weights based on clinical studies and evaluation of toxicity which include immobilized protein A quantity, volumes of plasma perfused and rate of administration, and preferred loading of the immobilized protein A in a cartridge.

Present Invention

Hence, this invention is directed to (a) an extracorporeal system and method for the immobilization of protein A (SPA) and therapy of patients with cancer; (b) guidelines for SPA volumes, quantities of plasma perfused and rate of administration; (c) loading of the protein A cartridge and its distributions; (d) a system and method of immobilization of protein A which may be employed to process very small quantities of a patient's sera; and (e) protein A perfused plasma for use by the host or others or storage in a bank for subsequent use.

SUMMARY OF THE INVENTION

In one aspect of the present invention, plasma is separated from the whole blood and perfused over SPA immobilized on a suitable inert support, preferably adsorbed in a collodion membrane closely adjacent to charcoal particles. The perfused plasma may then be recombined with the formed elements into whole blood and the whole blood perfused back into the circulation of the patient or stored for subsequent administration to other patients. Hence plasma may be collected from patients and processed over the immobilized protein A and administered to patients at different times. Thus, in addition, to the extracorporeal one step collection and following approach, plasma may be collected and administered to patients at different times. The present invention includes guidelines for the use of protein A based on clinical and toxicity evaluations to include immobilized protein A quantity, volumes of plasma perfused over immobilized protein A and the rate of administration of plasma perfused over immobilized protein A and administered to the patient.

Another aspect of the present invention is the provision of therapeutic, extracorporeal immobilized protein A as the immunoadsorbent and its manufacture. Preferably, protein A is immobilized in collodion membranes closely adjacent to activated charcoal, although it may be immobilized by other means and on other inert supports, as subsequently described. Preferably, the protein A particles should be physically separated from one another in the chamber housing.

Another aspect of the present invention is the discovery that a single non-toxic drug infusion, such as cytosine arabinoside (ARA-C), given intravenously at the conclusion of protein A perfusion results in a profound necrotizing tumoricidal response which far exceeds that due to this extracorporeal plasma perfusion of protein A or drug infusion alone. The magnitude, rapidity and specificity of the observed tumoricidal response with minimal host toxicity represents a potent and unique chemoimmunotherapeutic approach to breast adenocarcinoma and other carcinomas.

A further aspect of the present invention is a miniaturized protein A collodion-charcoal "frisbee" or column by which very small serum samples are processed.

A further aspect of the invention is the provision of protein A perfused plasma.

Other aspects of the invention appear throughout the specification and claims.

Accordingly, it is an object of the present invention to provide a therapeutic immunoadsorbent and guidelines for its use by which perfused plasma can be infused into patients with cancer safely and with therapeutic benefit to the patients.

A further object of the present invention is the provision of therapeutic, immobilized protein A (SPA) as the immunoadsorbent.

A further object of the present invention is the provision of protein A (SPA) immobilized in collodion membranes closely adjacent to charcoal.

A further object of the present invention is the provision of a system and method by which plasma is separated from the whole blood and perfused over such therapeutic immobilized protein A (SPA), then the perfused plasma is recombined with the formed elements into whole blood and the later is circulated back into the circulation system of the patients.

A further object of the present invention is the provision of and a method and system for providing protein A perfused plasma for treatment either of the plasma donor or others with the same cancer and which can be stored in banks for later use.

A further object of the present invention is the provision of guidelines for the safe and therapeutic use of protein A based for various body weights of patients including immobilized protein A quantity, volumes of plasma perfused and the rate of administration of plasma to the patient.

A further object of the present invention is the provision of a safe and therapeutically effective protein A cartridge including its loading, distribution and physical arrangement of protein A particles in the cartridge.

A further object of the present invention is the extracorporeal perfusion of plasma or non-extracorporeal perfusion of plasma over immobilized protein A followed by drug infusion to the patient during the immediate postperfusion period.

A further object of the present invention is the provision of a miniaturized therepeutic protein A immunoadsorbent which enables the processing of various small serum samples for testing.

Other and further featues, objects and advantages of the invention appear throughout the specification and claims.

DESCRIPTION OF PREFERRED EMBODIMENTS

Figure 1:
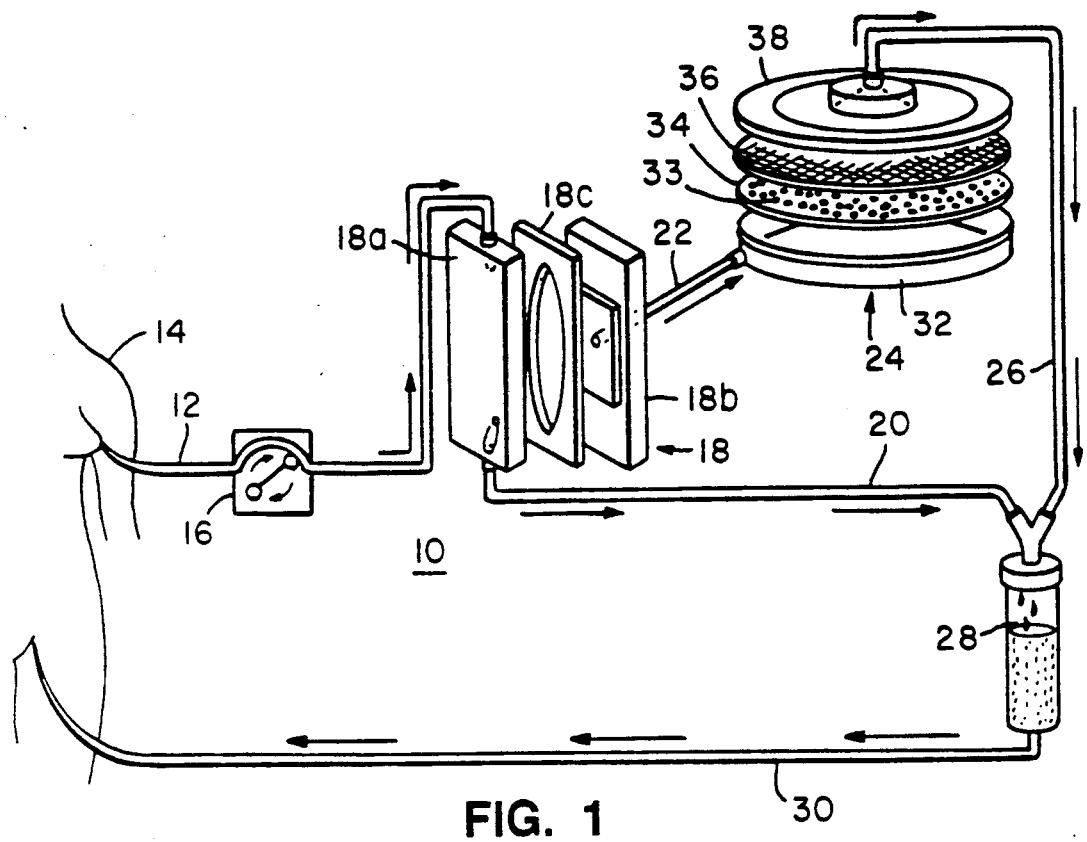
FIG. 1 is a schematic view of an extracorporeal immunoadsorption system utilizing a therapeutic protein A collodion charcoal immunoadsorbent according to the invention.

I have observed rapid and specific necrotizing tumoricidal reactions after plasma perfusion over immobilized protein A bearing staphylococcus (SPA). In addition, these tumoricidal responses can be further augmented with low dose chemotherapy given in the post treatment period.

In making the transition from canine studies to the treatment of patients with advanced breast adenocarcinoma, I discovered that perfusion of small volumes of plasma over non-covalently immobilized protein A (SPA) and administered to patients resulted in rapid, extensive and specific tumor killing responses. This resulted in a change of the treatment system from an elaborate system of on-line plasma-cell separation and immunoadsorption to one of perfusion of small volumes of plasma over immobilized protein A and adminstered to the patient.

In clinical studies toxicity was observed during the initial phases to include hypotension, tachycardia, pulmonary rales and diarrhea. As a result of a comprehensive evaluation of this toxicity, I discovered that the clinical toxicity could be reduced by controlling the following parameters: (a) quantities of protein A, (b) volumes of plasma perfused over immobilized protein A and delivered to the patient, (c) flow rates of plasma perfused over the immobilized protein A and delivered to the patient, and (d) treatment scheduling. This discovery is based upon careful studies which include recordings of clinical and seriological effects, blood pressure, heart rate, cardiac output, peripheral vascular resistance, and pulmonary vascular resistance and that the following treatment conditions and guidelines could reduce the cardiovascular toxicity while preserving the tumor killing effects of therapy: (a) immobilized protein A quantity ranging from about 0.12 mg to about 5.0 mg and preferably 0.6 mg adjusted for an adult spectrum of body weights and as little as 0.001-0.01 mg immobilized protein A for children, (b) volumes of 50 to 300 ml and preferably 50 ml of plasma perfused over the quantities of immobilized protein A and administered to adult patients and as little as 0.001 ml for children, (c) plasma flow rates of from about 2 to about 5 ml/min perfused over immobilized protein A and administered to patients, and (d) a treatment schedule preferably at every second or third day intervals.

I have also discovered criteria for the preparation of protein A immobilized on an inert carrier, such as charcoal. The immobilized protein A on the inert carrier, such as charcoal, must be loaded into a fluid bed in the chamber of the protein cartridge and each particle should be physically separated from one another to avoid coalescense and to enhance contact of the charcoal surface with the plasma perfused over it. Preferably, the immobilized protein A particles are distributed in a monolayer and it is also preferable that the protein A be immobilized by adsorption. These are of great importance since they effect (a) plasma flow distribution over the immobilized protein A, (b) plasma contact and reaction time with the immobilized protein A, (c) the rate of administration of plasma to the patient, and (d) the effectiveness of the immobilized protein A in generating therapeutic products.

Referring now to FIG. 1, an extracorporeal immunoadsorption system having immobilized protein A as the immunoadsorbent is illustrated and generally designated by the reference numeral 10. An inflow line 12 is connected from a vein or artery of the patient 14 and whole blood from a host 14, here shown as a patient with breast cancer is pumped by the pump 16 into a continuous flow cell separator 18, here shown as a filtration cell separator, which separates the whole blood into formed elements which flow into the line 20 and into plasma which flows in the line 22 to the therapeutic, extracorporeal immobilized protein A immunoadsorbent 24, as described in more detail later herein. The plasma then flows in the line 26 into the drip chamber and bubble trap 28, into which also flows the formed elements in the line 20 so that the formed elements and the plasma are combined into whole blood, which is returned in the outflow line 30 into a vein, here a femoral vein, not shown, of the patient 14.

The outflow line 12 and inflow line 30 are connected into veins of the patient 14 by catheters, not shown; although, the outflow line 12 can be connected by catheter to an artery of the patient 14.

Any desired type of non-pulsating pump can be used, such as Sarns Roller Pump, and the pump and the immunoadsorbent should be such as to permit adequate flow rates to prevent thrombogenicity or clotting of blood, and rates of 10 ml/min and above, such as 15-40 m/min through the system are satisfactory.

The protein A used herein was obtained from Pharmacia, Piscataway, N.J., and contained enterotoxins A, B, C, E, and F.

Any continuous flow plasma cell separator can be utilized, such as the filtration cell separator illustrated in FIG. 1 (Travenol, Morton Grove, Ill.) or for example, a centrifugal flow plasma cell separator (American Instruments Company, Silver Springs, Md.), in which whole blood is centrifuged at 1200-1500 Rev/minute.

The filtration cell separator in FIG. 1 is shown expanded and includes the body members 18a and 18b and the gasket 18c. The body members include membranes, not shown, operative for the blood to flow out through the line 20 and the plasma to flow through into the line 22. Any desired cell separator can be used, a number of which are readily available on the market.

Figure 3:
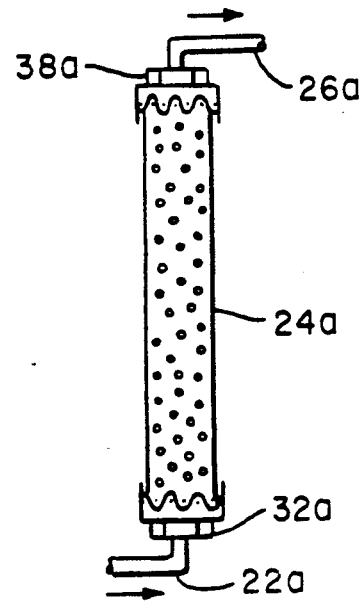
FIG. 3 is a fragmentary, elevational view of an alternate therapeutic, extracorporeal protein A collodion-charcoal immunoadsorbent column according to the invention.

The therapeutic, extracorporeal immobilized protein A immunoadsorbent can take a variety of forms, here shown as a flat or "Frisbee" form in FIG. 1, or, for example, as a column 24a as illustrated in FIG. 3.

Referring to FIG. 1, the "frisbee" cartridge of immunoadsorbent 24 is shown expanded for purposes of illustration and includes a lower pan or flat cylindrical-like body member 32 into which is placed a stainless steel mesh disc 33 upon which are placed particles of protein A immobilized on inert support particles, preferably charcoal by collodion, 34. Placed on top of the particles of immobilized protein A 34 is another stainless steel mesh screen disc 36 and an upper flat or pancake-like lid or body member 38 is disposed above the screen 36.

In assembling the immunoadsorbent cartridge 24, the particles of protein A immobilized on an inert support, preferably activated charcoal by collodion 34, are loaded into a fluid bed and settle on the screen 33 placed in the bottom body member 32, the disc screen 36 is placed above them and the upper body member or lid 38 is then clamped down with its edges over the lower body member 32 thereby completely enclosing the immunoadsorbent particles 33 and screens 32 and 34 into the immunoadsorbent cartridge 24.

In use, the separated plasma enters the therapeutic immunoadsorbent cartridge 24 through the line 22 and flows through the screen 32, the immobilized protein A immobilized on the inert support particles 33, the screen 26 and then out the outflow line 26 into the drip and bubble chamber 28.

Referring now to FIG. 3, a modified form of the therapeutic extracorporeal immunoadsorbent cartridge 24a in column form is illustrated. In this modification, the body is of tubular shape into which is placed the particles of immobilized protein A on an inert support, preferably collodion immobilized on activated charcoal particles, stainless steel filters, not shown, are provided at each end, and the tubular body is closed at the lower and upper ends by the closure members 32a and 38a, respectively, into which the inflow plasma line 22a and outflow plasma line 26a extend.

Figure 5:
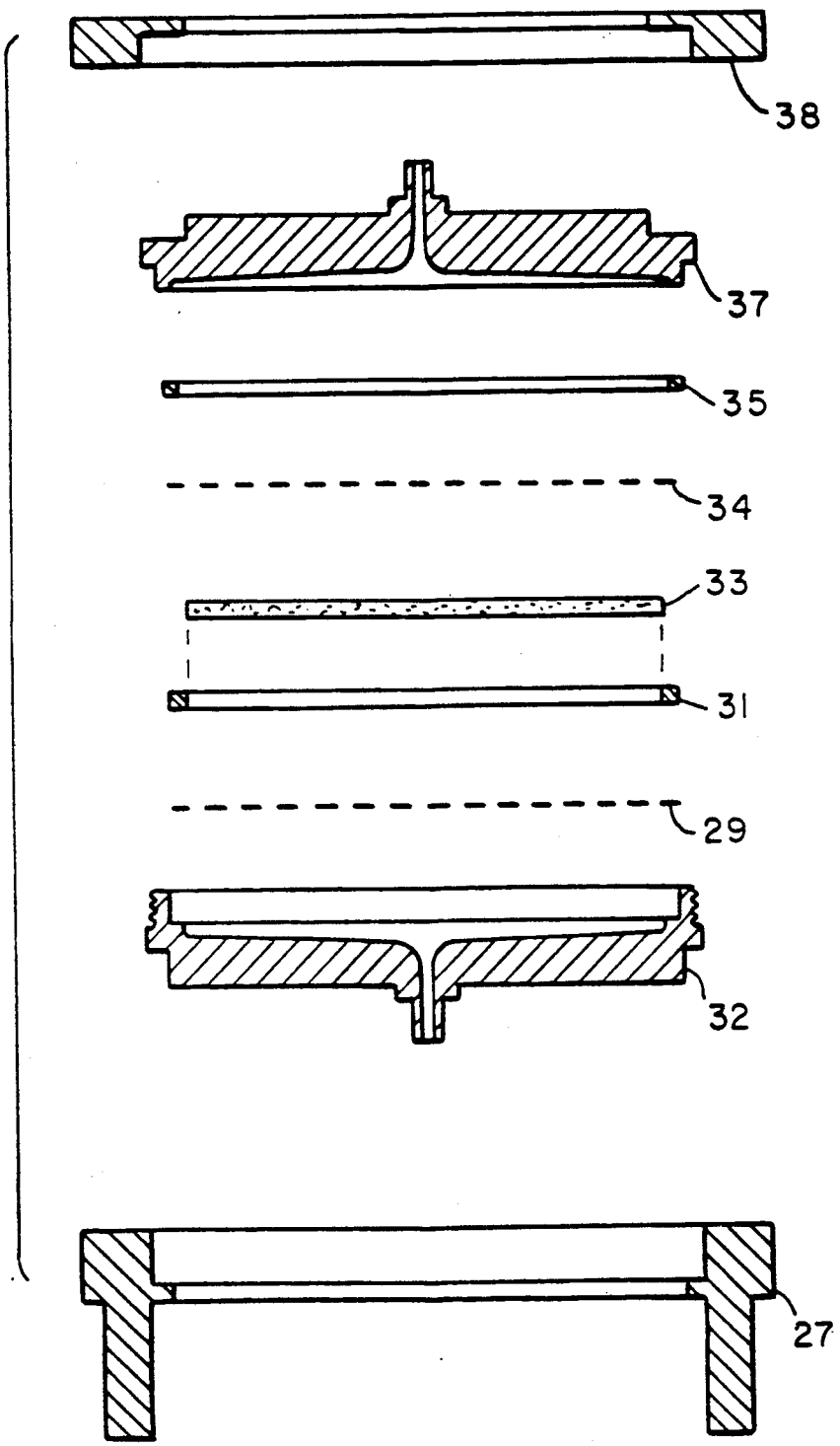
FIG. 5 is an expanded view of the therapeutic protein A cartridge of FIG. 4.

The therapeutic, extracorporeal immunoadsorbent cartridge may take a variety of forms, the presently preferred embodiment being the "frisbee" from illustrated in FIG. 5.

The screens 33 and 36, as well as those not shown in the column 24a, should have a mesh size in the range of from about 40-80 mesh.

Figure 4:
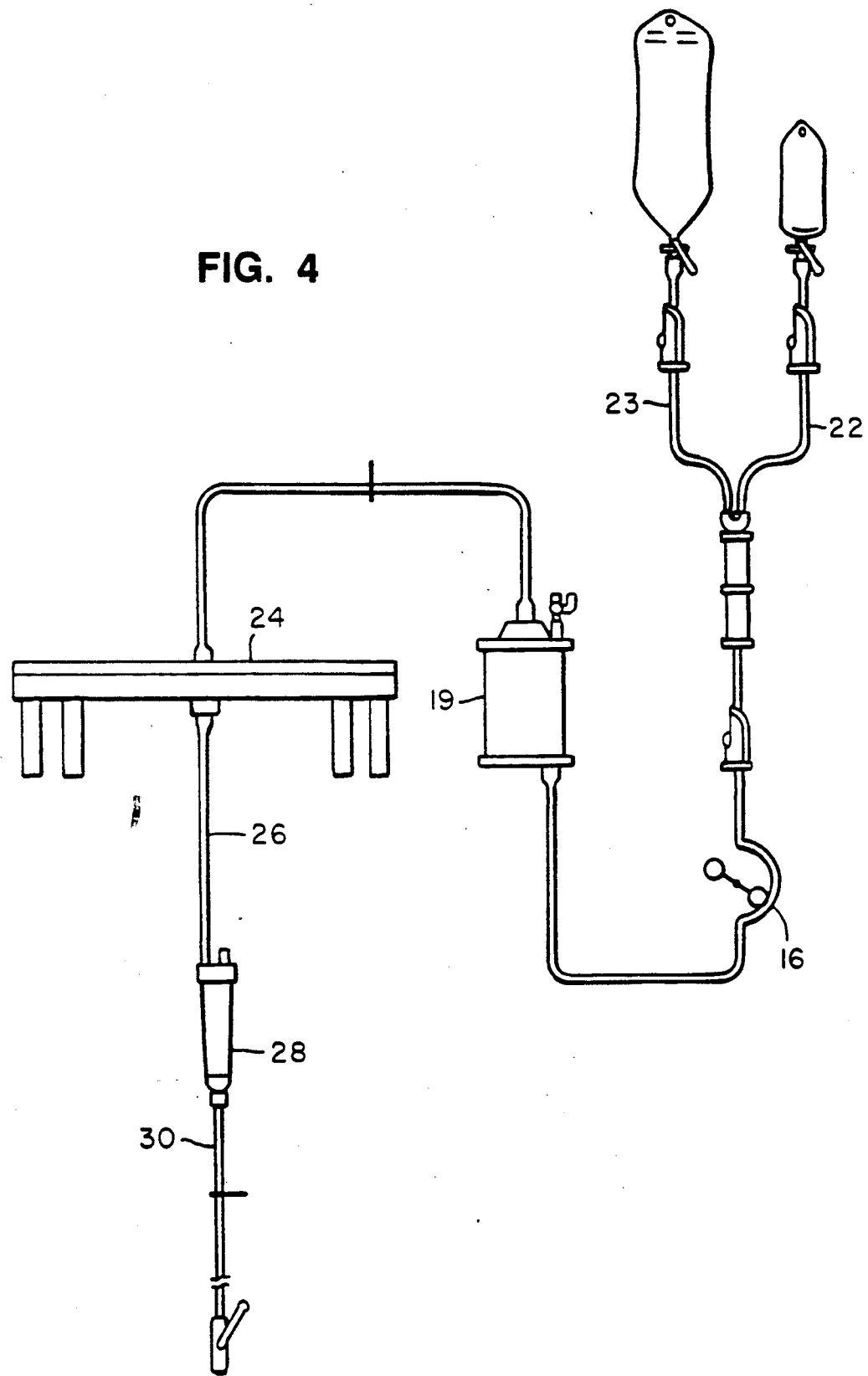
FIG. 4 is a schematic view of another embodiment of the extracorporeal immunoadsorption system.

Referring now to FIGS. 4 and 5 a modified form of the plasma perfusion system is illustrated. This system is essentially the same as the system previously described, however, it does illustrate as inlets an inflow plasma line 22 and an inflow saline line 23, as well as a filter 19.

FIG. 5 is an expanded view of a protein A cartridge which includes the frame top 38, cartridge top 37, gasket 35, screen 34, immobilized protein A on charcoal 33, spacer 31, bottom screen 29, cartridge bottom 32 and frame bottom 27. The protein A cartridge is assembled simply by securing the parts together as illustrated in FIG. 5.

The preferable immunoadsorbent is prepared by washing activated charcoal, preferrably of vegetable origin such as coconut charcoal, 6-16 mesh (Fischer Scientific Company, Fairlawn, N.J.), extensively with distilled water and placing the charcoal particles under suction in order to remove debris and fines and then thoroughly drying the charcoal particles. The dried charcoal particles are then placed in a container, care being taken in the transfer process to avoid abrasion of the charcoal particles. The charcoal is added to a solution of collodion, ether and alcohol and protein A. The ether and alcohol are absorbed by the charcoal thereby immobilizing protein A in collodion membranes closely adjacent to and on the activated charcoal particles. The particles are then added to a beaker of normal saline and loaded into the immunoadsorbent cartridge 24 which has been pre-filled with fluid by the saline line 33. The particles are physically distributed in a monolayer, flat disc or in the column 24a in the form of a column, as previously described. It is important that the immobilized protein A particles be premoistened before loading into the immunoadsorbent chamber and that the particles be loaded into a fluid filled chamber and be permitted to settle through the fluid onto the screen 29. It is also important that the particles be physically separated from one another in the chamber and immobilized on the support.

The protein A collodion-charcoal immunoadsorbent has the following important characteristics: (1) it is bicompatible and incorporates large quantities of protein A in its membranes, (2) the protein A collodion-charcoal presents a large surface to volume ratio so that a small extracorporeal volume of plasma may contact a large immunoadsorption surface, (3) the binding of protein A in collodion on charcoal is sufficiently firm to prevent release thereof into the circulation, (4) the collodion-charcoal support is structurally stable to avoid embolization of the structured material into hosts, (5) the support and immobilized protein A are minimally thrombogenic to prevent clotting, and finally (6) protein A collodion-charcoal has low non-specific adsorption characteristics and allows adequate flow rates of plasma through it.

While protein A (SPA) immobilized by collodion membranes on activated charcoal is preferred, protein A can be immobilized by other means on other support particles,, for example, by irreversible covalent coupling adsorption, physical entrapment or by chemical or physical means readily available on other inert or derivatized support particles including synthetic materials, such as nylon, methacrylate, polystyrene, and other plastic and natural inert particles.

The following examples I and II described presently preferred methods of preparing the preferred therapeutic, extracorporeal protein A collodion-charcoal immunoadsorbent.

EXAMPLE I

In order to remove fines, debris, organic material and other contaminants, charcoal was treated in the following fashion. 350 grams of 6-16 mesh charcoal (Fischer) was poured into a No. 6 mesh screen and sieved into a No. 16 mesh screen. The large charcoal in the No. 6 mesh screen was discarded and the charcoal in the No. 16 mesh screen was poured into a 100 ml beaker. The charcoal in the beaker was washed by a tube in the bottom with 8 L of non-pyrogenic sterile water. The charcoal was then poured in a water slurry into an sterile liter bottle leaving about 5" of water above the top of the charcoal and then it was autoclaved for 20 minutes.

The autoclaved charcoal was then washed with 4 L of nonpyrogenic sterile water, placed in a dessicator under vacuum for 15 minutes, and washed with 4 L of non-pyrogenic water. The charcoal was then dessicated under vacuum for 15 minutes, washed with 10 L of non-pyrogenic sterile water and the water slurry of charcoal was covered with a clean drape and dried overnight at 200° F.

Using sterile instruments, the charcoal was aliquoted into 30 g aliquots being careful not to scrape the charcoal on the bottom of the sieve to avoid the creating of fines. The aliquots were packed in towels, autoclaved for 40 minutes and dried in an oven overnight at 150° F. With this procedure most fines and debris were removed from the activated charcoal and the charcoal particles were now ready to be treated with the protein A collodion solution.

EXAMPLE II

For coating of charcoal with protein A collodion, a solution of 0.15M Tris buffer pH 7.4, was dissolved in 200 ml of sterile water, pH 7.4. In a beaker, 4.1 ml of absolute alcohol was added with 4.1 ml of collodion and 40 ml ether. 5 mg protein A in 0.5 ml 0.15M Tris was added to the beaker. The stirbar was then removed with sterile forceps and 30 grams of the processed charcoal was added to the beaker and gently stirred under a vacuum hood until the charcoal was dry The charcoal was then placed in a sterile pyrex drying pan and dried in a hood overnight under ultraviolet light.

The resulting therapeutic, immunoadsorbent consisted of protein A immobilized in collodion membranes bound closely adjacent to the surface of the activated charcoal particles and had all of the desirable properties and characteristics set forth above.

While activated coconut charcoal is particularly suited and preferred, charcoal, particularly activated charcoal of vegetable origin is satisfactory.

EXAMPLE III

This example illustrates the application of the system and method to dogs. Twelve dogs with various spontaneous solid tumors were treated for one hour by extracorporeal perfusion over protein A bearing staphylococcus aureus Cowans I. All dogs showed a necrotizing reaction with some associated healing of ulcerated tumorous lesions.

EXAMPLE IV

In this example, the plasma perfusion system of Example III was revised by immobilizing purified protein A in a collodion charcoal matrix. Preclinical investigations with protein A collodion charcoal system were made in dogs with various spontaneous neoplasms. These studies were done under conditions which would closely simulate those which were to be subsequently employed in patients. Dogs were sedated and whole blood was pumped into a continuous flow plasma cell separator where it was partitioned into formed elements and plasma. Plasma (1 calculated plasma volume) was then selectively circulated at flow rates of 5-20 ml/min over a protein A collodion charcoal column containing 5-10 mg of immobilized protein A. The plasma emerging from the column was then reunited with formed elements and passaged back to the dog by a peripheral vein. Summary of the acute tumoricidal reactions observed in 8 dogs within 12 hours after treatment are shown in Table 1.

verted spontaneously to normal. All dogs had baseline temperature levels within 12 hours after treatment.

(c) Blood chemistries in 4 dogs before 12-48 hours after treatment are shown in Table 2. There were no significant changes in the parameters measured.

(d) Protein A charcoal unit: All charcoal units were disassembled and visually examined at the conclusion of treatment. There was no visual evidence of plasma protein precipitate or other physical changes.

EXAMPLE V

Five patients, ages 52-62 years, underwent treatment (Table 2). Patients #1, #2, #4 and #5 had recurrent breast adenocarcinoma 6 months to 3 years after mastectomy. At the time of initiation of immunotherapy, all patients had chest wall tumor which was fixed to underlying fascia and/or muscle. Patients #1-#4 had supraclavicular lymph node extension of tumor. Patient #1 had metastatic lesions in right humerus, tibia and fibula and patient #2 had diffuse bilateral lung and pleural metastases with bilateral pleural effusions. Associated medical conditions in all patients are shown in Table 3. Before beginning treatment, each patient had a physical examination, complete blood count, studies of liver and renal function, measurements of blood calcium, uric acid, total protein and albumin, chest roentgenogram, mestastic skeletal survey and radionuclide scans of liver, spleen and bones. Tests were repeated at appropriate intervals to evaluate response to therapy. Microscopic and ultrastructural evaluation of tumor tissue was undertaken on tumor biopsy specimens obtained before and at various intervals after treatments by previously described methods.

TABLE 1

REACTIONS IN TUMORS AFTER PLASMA PERFUSION OVER PROTEIN A COLLODION CHARCOAL

| Dog # | Breed | Sex | Tumor Histology | Location of Indicator Lesion* | Gross Morphology of Tumors (12-48 Hours After Treatment)** | |
|---|---|---|---|---|---|---|
| | | | | | Hyperemia | Necrosis |
| 1 | Poodle | F | Mammary Adenocarcinoma | Chest wall | 4+ | 4+ |
| 2 | Collie | F | Fibrosarcoma | Chest wall | 4+ | 4+ |
| 3 | Whippit | F | Mammary Adenocarcinoma | Chest wall | 4+ | 4+ |
| 4 | Poodle | F | Hemangiosarcoma | Chest wall | 4+ | 4+ |
| 5 | Bloodhound | F | Mammary Adenocarcinoma | Chest wall | 3+ | 3+ |
| 6 | Collie | F | Mammary Adenocarcinoma | Chest wall | 3+ | 3+ |
| 7 | German Shepherd | F | Mammary Adenocarcinoma | Chest wall | 2+ | 2+ |
| 8 | Cocker Spaniel | F | Mammary Adenocarcinoma | Chest wall | 2+ | 2+ |

Sum of products of perpendicular diameters of indicator lesions ranged from 8.2 to 35.
**Hyperemia and Necrosis graded by 2 observers as 0 = none, 1+ = mild, 2+ = moderate, 3+ = severe, 4+ = very severe.

TOXICITY (a) General condition of animals after treatment: All dogs appeared normal and were ambulating and eating within 4 hours after treatment. Dogs showed no evidence of lethargy or behavioral changes when re-evaluated 12 hours later.

(b) Rectal temperature elevations of 1.3°-2.5° F. above pretreatment levels were observed in 3 dogs which hours after treatment and then reverted spontaneously lasted 2-3 hours after treatment and then re-

TABLE 2

CLINICAL CHARACTERISTICS OF PATIENTS

| Patient No. | Age (Yrs) | Weight (kg) | Previous Therapy | Tumor Sites Involved | Associated Disease or Conditions |
|---|---|---|---|---|---|
| 1 | 57 | 90 | Mastectomy, Radiotherapy, CMF, D, A | Chest Wall, Supraclavicular Lymph Nodes, Bones | Laennec's Cirrhosis, Diabetes Mellitus, Thrombocytopenia |
| 2 | 52 | 61 | Mastectomy, CMF, D | Chest Wall, Lungs | None |
| 3 | 52 | 140 | Radiotherapy, CMF, D, V, TC, FLX | Chest Wall Supraclavicular Lymph Nodes | None |
| 4 | 60 | 60 | Mastectomy, Radiotherapy, CMF, D, V, TC, FLX, MA | Chest Wall Supraclavicular Lymph Nodes | None |

TABLE 2-continued

| | | | CLINICAL CHARACTERISTICS OF PATIENTS | | |
|---|---|---|---|---|---|
| Patient No. | Age (Yrs) | Weight (kg) | Previous Therapy | Tumor Sites Involved | Associated Disease or Conditions |
| 5 | 62 | 60 | Mastectomy, Radiotherapy, TC | Chest Wall | Osteoporosis |

CMF = Cyclophosphamide, Methotrexate, 5-Fluorouricil
D = Doxorubicin
A = Alkeran
V = Vincristine
TC = Tamoxifen Citrate
FLX˙ = Fluoxymesterone
MA = Megastrol Acetate Tumor Measurements and Response Criteria Measurements of tumor mass were made before and at least 3 times weekly after treatment began. Tumor diameters were measured a long 2 axes, one being the longest and the other the longest perpendicular to it by a minimum of 2 investigators and the sum of the products of the tumor diameters was determined. The criteria for responses were modifications of those adopted by the International Union Against Cancer. Partial remission was at least a 50% decrease in the product of diameters in measurable lesions. No lesion could have progressed nor any new lesion appear, but every lesion need not have regressed for qualification for partial remission. Less than partial remission or improvement idicated a 25% to 50% decrease in measurable lesions. Stable disease was defined as less than 25% decrease or a less than 25% increase in the size of measurable lesions and progressive disease as greater than or equal to a 25% increase in size of any lesion or appearance of new lesions.

Plasma Perfusion Systems

Protein A (Pharmacia, Piscataway, N.J.) 0.125 mg, 0.6 mg, 1.25 mg, or 5 mg, were immobilized in 30 grams of collodion-charcoal by a modification of previously described techniques (5-8). Protein A collodion charcoal (PACC) particles were placed in a monolayer between 40 mesh screens and washed with saline (7000 ml). Microbiologic cultures, linulus and rabbit pyrogen tests in sale wash effluent from PACC were negative (9,10). A cartridge containing PACC was positioned on the plasma line of a continuous flow plasma-cell separator (American Instrument Company, Silver Spring, Md.). Whole blood was pumped from the subclavian vein into a continuous flow plasma-cell separator where it was partitioned into formed elements and plasma. Separated plasma was first pumped through 0.45 micron pleated membrane filter, then through the PACC column at flow rates of 10-20 ml/min after which it rejoined the formed elements and was returned into a peripheral vein.

In other studies the cell separation unit was not employed; instead plasma infusion treatments were carried out with plasma which was collected by phlebotomy of whole blood from patients or donors. Formed elements were returned and plasma was stored in 50 ml aliquots in citrate phosphate dextrose anticoagulant at −20° C. For treatments, plasma in 20-200 ml volumes was first passaged through a 0.45 micron pleated filter, then over PACC at flow rates of 2-20 ml/min and returned to the patient intravenously. Saline, 700 ml, was then infused through the system to clear the circuit of plasma.

Treatment Conditions

Table 3 gives treatment schedules, protein A quantities employed, volumes of plasma utilized and rate of plasma administration.

TABLE 3

| | TREATMENT CONDITIONS | | | | |
|---|---|---|---|---|---|
| Patient No. | No. Of Treatments | Duration Of Treatment (Days) | Protein A Quantity (mg) | Plasma Volumes Perfused (ml) | Plasma Flow Rates (ml/Min) |
| 1 | 12 | 123 | 5 | 100-300 | 20-30 |
| 2 | 1 | 1 | 5 | 100 | 20 |
| 3 | 5 | 9 | 1.25 | 100 | 2-5 |
| 4 | 18 | 58 | 0.12-0.6 | 5-50 | 2-5 |
| 5 | 8 | 28 | 1.25 | 100-150 | 2-5 |

RESULTS

Clinical and Morphologic Findings After Perfusion of Autologous Plasma Over PACC Patient #1 was treated first by extracorporeal perfusion of 200 ml of autologous plasma over 5 mg of immobilized protein A. Twenty minutes after the completion of perfusion, the patient experienced pain in tumor sites on chest wall and supraclavicular lymph nodes as well as right humerus. In the next 2 hours, tumor in chest wall and supraclavicular lymph nodes became hyperemic and edematous. Within 48 hours, multiple spontaneous ulcerations appeared on the chest wall tumor surface while the contralateral normal breast showed no inflammatory reaction. Chest wall and left supraclavicular lymph nodes became less adherent to underlying tissue. Microscopic and ultrastructural evaluation of tumor tissue 48 hours after treatment confirmed the presence of diffuse tumor cell necrosis with minimal inflammatory cell infiltration. The rapidity of onset of this tumoricidal reaction and the absence of inflammatory cells in the lesion after treatment suggested that plasma-borne tumoricidal factor(s) were activated after contact of plasma with PACC. Hence, patient #1 underwent phlebotomy on 2 occasions in which a total of 1000 ml of plasma was collected. On 5 occasions, at 5-14 day intervals, this plasma was perfused in 100 or 200 ml volumes over PACC and returned to the patient intravenously. Shortly after each of these treatments, the patient experienced pain in tumor sites in chest wall, supraclavicular lymph nodes and right humerus; hyperemia and edema were present in chest wall and supraclavicular lesions. Forty-two days after the commencing immunotherapy (total of 5 treatments), there was a 60% reduction in tumor dimensions (Table 5). Following a total of 12 treatments given over a 123 day period, there was a 79.8% reduction of tumor dimensions (Table 4). There was nearly total disappearance of a metastatic supraclavicular lymph node after the 6th treatment. Pain present before beginning treatment at metastatic sites in right humerus; radioisotopic scan of the bones done 59 and 109 days after treatment showed densities in metastatic sites similar to those observed before treatment with no progression or dissemination.

went an additional 12 treatments over a 45 day period, during which the tumor regression was sustained. Microscopic examination of tumor tissue 17 days after commencing treatment showed necrosis of tumor cells and numerous tumor cell ghosts.

Clinical and Morphologic Findings After Perfusion Homologous Plasma Over PACC

To determine whether plasma from patient #1 which induced a tumor regression after passage over PACC, could be transferred and induce a similar response in another patient with breast adenocarcinoma, patient #5 was treated with plasma obtained from patient #1 and 2 additional patients with advanced breast adenocarcinoma. Ten to 20 minutes after each of these treatments, the patient experienced pain localized in the chest wall tumor which became hyperemic, edematous and tender

TABLE 4
RESPONSE TO TREATMENTS

| Patient No. | No. Of Treatments | Response To Treatment | Product of Perpendicular Diameters | | |
|---|---|---|---|---|---|
| | | | Pretreatment | Post-Treatment | Percent Reduction |
| 1 | 12 | Partial Remission (123*) | 183.0 | 37.0 | 79.7 |
| 2 | 1 | None | | | |
| 3 | 5 | Less Than Partial Remission Or Improvement (10) | 155.8 | 104.1 | 33.1 |
| 4 | 18 | Partial Remission (58**) | 42.2 | 15.1 | 66.6 |
| 5 | 8 | Partial Remission (44) | 33.6 | 14.3 | 57.4 |

*Objective partial remission of 60% was noted after 5 treatments or 42 days following immunotherapy.
**Objective partial remission was observed after 6 treatments or 13 days following immunotherapy.

Patient #2 was treated once by perfusion of 100 ml of autologous plasma over 5 mg of immobilized protein A. She experienced pain, hyperemia and edema of chest wall lesions shortly after concluding treatment. While there was reduction in the number of cutaneous nodules present in the chest wall, objective regression in chest wall tumor could not be discerned in the ensuing 7 days; pulmonary lesions could not be evaluated because of the presence of bilateral pleural effusions.

To assess the effects of lower doses of immobilized protein A on therapeutic response, 1.25 mg and 0.6 mg of immobilized protein A were employed for treatments in patients #3 and #4 respectively compared to 5 mg in patient #1. In addition, treatments were scheduled at more frequent intervals (2 or 3 days) compared to patient #1. Shortly after each perfusion, patient #3 experienced severe pain associated with hyperemia and edema localized in tumor on chest wall and supraclavicular lymph nodes which lasted for several days after treatment. Tumor necrosis was evident in a large ulcerating tumor site on the breast after each treatment. After completing 5 treatments over a 9 day period, there was a reduction of 33.1% in tumor dimensions (Table 5) which was associated with a loss of adherence of tumor to the underlying chest wall. The controlateral normal breast showed no inflammatory response during treatment. Microscopic examination of tumor tissue after 5 treatments showed extensive necrosis of neoplastic cells and numerous tumor cell ghosts. Patient #4 underwent 6 treatments in which 50 ml of pretreatment plasma was passaged over 0.6 mg of immobilized protein A. She experienced acute reactions in her tumor after each treatment similar to patient #3. Thirteen days after commencing treatment, she had a 66.6% reduction in tumor dimensions (Table 5) wall. This patient under-over the ensuing 12 hours. There was no reaction in the contralateral normal breast. Forty-four days after beginning therapy (total of 8 treatments), there was a 57.4% reduction in tumor diameters (Table 4).

Toxicity

A summary of clinical toxicity observed in these 5 patients is given in Table 5. Within 5 to 30 minutes after completion of most plasma perfusion treatments, patients experienced chills with subsequent temperature elevations, tachycardia and moderate to severe pain located to tumor sites on the chest wall which, in some instances, lasted for several days after treatment. The most severe toxicity was experienced in the 2 patients whose plasma was perfused over the highest quantity of protein A. In patient #1, hypotension occurred in 6 of 12 treatments, nausea and vomiting in 9. This patient also showed the highest mean temperature elevation and developed pulmonary rales on 2 occasions. When it occurred, hypotension was managed with fluids, colloid, vasopressors or a short course of corticosteroid therapy. Patient #2, whose plasma was also perfused over 5 mg of immobilized protein A, had extensive lung metastases of her breast adenocarcinoma with bilateral pleural effusions. During her first treatment, she developed acute bronchospasm with pulmonary rales which was reversed with bronchodilators and corticosteroid treatment.

When immobilized protein A dose was lowered to 1.25 mg or 0.6 mg in patient #3, #4, and #5, episodes of hypotension, nausea, vomiting were reduced and pulmonary rales were not observed. Temperature elevations and tachycardia occurred but were not as severe as in patient #1.

pressed as dynes-sec-cm$^{-5}$); Stroke Volume=Cardiac Output/Heart Rate.

TABLE 5

CLINICAL TOXICITY

| Patient No. (N = Number Treatments Evaluated) | Protein A Quantity Immobilized (mg) | Hypotension: Systolic BP 80 mmHg (Number of Episodes) | Cardiac Rate (Change From Preperfusion) | Temperature (Change From Preperfusion) | Rigor, Chills | Nausea, Vomiting, Diarrhea (Number Of Episodes) | Pulmonary Rales |
|---|---|---|---|---|---|---|---|
| 1 (N = 12) | 5 | 6 | 47 ± 10 | 2.85 ± .05 | 12 | 9 | 2 |
| 2 (N = 1) | 5 | 0 | 55 ± 0 | 1.30 ± .0 | 1 | 0 | 1* |
| 3 (N = 5) | 1.25 | 0 | 29 ± 5 | 1.75 ± .06 | 4 | 0 | 0 |
| 4 (N = 18) | 0.12–0.6 | 1 | 24 ± 12 | 0.94 ± .75 | 10 | 9 | 0 |
| 5 (N = 8) | 1.25 | 1 | 40 ± 5 | 1.98 ± .09 | 7 | 0 | 0 |

*Wheezing also present

Cardiovascular Toxicity Studies: For invasive hemodynamic studies, patients under right heart catheterization with a #7 French Swan-Ganz, ballon-tipped thermal-dilution catheter (Edwards Laboratories, Chicago, Ill.) after percutaneous puncture of a subclavian vein. The catheter was appropriately positioned in the pulmonary artery. A Teflon arterial catheter (Intracath, Chicago, Ill.) was placed in a peripheral artery and connected to a strain gauge pressure transducer. Intracardiac and systemic blood pressures, electrocardiographic tracing and rectal temperature were displayed continuously on a bedside multigraph recorder (Mennen Gratebach, Chicago, Ill.). Mean pressures were obtained by electronic integration and heart rate was determined from the electrocardiographic signal. The mid-axillary line was defined as the 0 pressure reference level. For some treatments, arterial blood pressure was determined by arm-cuff and mercury manometer. In these instances, mean blood pressure was calculated by adding ⅓ of the pulse pressure to the diastolic blood pressure. Rectal temperature readings were monitored continuously with a rectal probe. An average of three cardiac output determinations was made by thermal dilution technique. Data recorded included mean right atrial pressure (RAP), pulmonary artery pressure (PAP), mean pulmonary artery pressure (PAP), mean pulmonary capillary wedge pressure (PCW), systolic (S), diastolic (D) and mean (BP) arterial blood pressure (BP). Hemodynamic indices were derived from pressure and cardiac output data according to the following standard formulae: Systemic vascular resistance (SVR)=80 (BP)−(RAP)/Cardiac Output both ex- Baseline hemodynamic parameters were obtained at 5 minute intervals 3 to 5 times before beginning plasma infusion treatments. During infusion, aforementioned parameters were measured every 5 minutes for the first 90 minutes and subsequently ever 10 to 15 minutes for an additional 6 hours. Parameters were then measured every 30 to 60 minutes for the ensuing 18 to 24 hours.

Definition of Initial and Modified Treatment Conditions: Table 6 defines the characteristics for treatment conditions. A total of 14 treatments were carried out under the initial conditions, 12 in patient #1, 2 in patient #5. For the initial treatment program, 1.25 mg or 5 mg of immobilized protein A was used, with plasma volumes of 100 to 300 ml infused at flow rates of 20 to 30 ml/min. Modified treatment conditions were employed in 3 patients for a total of 32 treatments. These conditions were as follows: reduced quantities of protein A (0.6125 mg to 1.25 mg), smaller volumes of plasma infused (5 to 150 ml), and slower infusion flow rates (2 to 5 ml/min) (Table 7).

TABLE 6

INITIAL AND MODIFIED TREATMENT CONDITIONS

| Group | Number Of Treatments Evaluated | Protein A Immobilized (mg) | Plasma Volume Infused (ml) | Infusion Flow Rate (ml/min) |
|---|---|---|---|---|
| Initial Treatment Conditions: | N = 12 | 1.25–5 | 100–300 | 20–30 |
| Modified Treatment Conditions: | N = 32 | 0.625–1.25 | 5–150 | 2–5 |

TABLE 7

TREATMENT CONDITIONS

| Patients | Number of Treatments Initial Conditions | Number of Treatments Modified Conditions | Treatment Interval (days) | Length Of Treatment (days) | Plasma Volume Infused (ml) | Infusion Flow Rate (ml/min) | Protein A Quantity Immobilized (mg) |
|---|---|---|---|---|---|---|---|
| #1 | 12 | 0 | 5–17 | 123 | 100–300 | 20–30 | 5 |
| #3 | 0 | 5 | 2–3 | 9 | 50 | 5 | 1.25 |
| #4 | 0 | 18 | 1–5 | 58 | 5–50 | 2–5 | 0.6–1.25 |
| #5 | 2 | 9 | 2–7 | 60 | 100 | 5–20 | 1.25 |
|  | 14* | 32 |  |  |  |  |  |

*2 treatments excluded from analysis

Initial Treatment Conditions: Summarization of the reaction characteristics for 12 treatments performed utilizing the initial treatment conditions was as follows: Mean blood pressure and mean pulmonary artery pressure at first increased slightly with subsequent decline. Concomitant with the diminished pressures was a tachycardia with pulse rate increasing from 93±10 beats/min (mean±standard deviation for 12 treatments) to 135±15 beats/min. Cardiac output also increased from 6.5±1.2 L/min to 9.8±2.5 L/min. The systemic vascular resistance declined from 1200±150 dynes-sec-cm$^{-5}$ to 620±75 dynes-sec-cm$^{-5}$. Total pulmonary vascular resistance was also diminished. Stroke volume initially increased as the cardiac output rose, however subsequently decreased despite the cardiac output remaining elevated over the baseline level. Rectal temperature for the group rose to approximately 39°±1.5° C.

Modified Treatment Conditions: Table 8 summarizes the maximum and minimum parameter changes during immunoperfusion for this group treated with modified conditions and compares them to the group treated under initial conditions. Generally, there were fewer cardiovascular changes when the modified treatment conditions were employed. Specifically, maximum heart rate was 144±8 beats/min compared to 122±15 beats/min ($p<0.001$). The lowest systemic vascular resistance reached in the modified treatment group was 1063±112 dynes-sec-cm$^{-5}$, $p<0.005$). Indeed, there was a 53% fall from baseline for the initial group compared to a 25% decline in the modified treatment group ($p<0.005$). The mean blood pressure in the modified treatment group fell to only 77±11 mmHg compared to 59±14 mmHg in the initial treatment group, ($p<0.001$). Additionally, the maximum rectal temperature noted in the modified treatment group was only 38.3°±0.9° C. vs. 40°±0.5° C. ($p<0.001$) for the initial treatment group conditions.

nafcillin; however, she lapsed into hepatic coma shortly after oral feedings were begun and expired 4 weeks after her last treatment. Autopsy showed a small liver (1000 gms) containing extensive micronodular Laennec's cirrhosis, with cholestatis (possible induced by nafcillin) and no evidence of hepatic metastases. Her breast adenocarcinoma in the chest wall and supraclavicular lymph nodes were markedly reduced from pretreatment size and largely replaced by connective tissue. Very small microscopic foci of tumor were found in right lung, thyroid and pituitary which were undetectable by clinical, laboratory and roentgenographic studies while the patient was undergoing immunotherapy. Patient #2 with diffuse metastatic lung disease was given radiation after immunotherapy but died 6 weeks later of her extensive pulmonary disease.

EXAMPLE VI

In this example, a synergistic effect between protein A collodion charcoal (PACC) and drug infusion was obtained. Spontaneous mammary adenocarcinoma occurs commonly in adult female dogs and is considered to represent an excellent model of human breast adenocarcinoma. The observed tumoricidal response ob-

TABLE 8
CARDIOVASCULAR CHANGES DURING IMMUNOPERFUSION:
Initial vs Modified Treatment Conditions

| Parameter | Initial Treatment Conditions (N = 12) | Modified Treatment Conditions (N = 32) | p Value (% change) |
|---|---|---|---|
| Lowest Systolic BP (mmHg): | 103 ± 8** | 111 ± 14 | $p < .001$ |
| % | −42 ± 10 | −14 ± 8 | |
| Lowest Mean Bp (mmHg): | 59 ± 14 | 77 ± 11 | $p < .001$ |
| % | −46 ± 12 | −16 ± 8 | |
| Lowest Mean PAP (mmHg): | 18 ± 7 | 13 ± 11 | $p = NS$ |
| % | −41 ± 14 | −38 ± 23 | |
| Lowest LV Filling Pressure (mmHg): | 6 ± 4 | 5 ± 4 | $p = NS$ |
| % | −63 ± 19 | −48 ± 37 | |
| Maximum Cardiac Output (L/min): | 11.0 ± 2.0 | 7.03 ± 1.09 | $p < .05$ |
| % | 64 ± 17 | 21 ± 16 | |
| Lowest SVR (dynes-sec-cm$^{-5}$): | 536 ± 66 | 1063 ± 112 | $p < .005$ |
| % | −53 ± 8 | −25 ± 8 | |
| Lowest TPR (dynes-sec-cm$^{-5}$): | 146 ± 44 | 158 ± 109 | $p = NS$ |
| % | −44 ± 14 | −41 ± 13 | |
| Maximum Heart Rate (beats/min): | 144 ± 8 | 122 ± 15 | $p < .001$ |
| % | 56 ± 17 | 28 ± 15 | |
| Maximum Rectal Temp (°C.) | 40 ± 0.5 | 38.3 ± 0.9 | $p < .001$ |
| % | 8 ± 2 | 3 ± 2 | |

*% change from baseline value
**Mean ± SD of group

Present Status of Patients

Patients #3, #4 and #5 are presently alive and clinically stable. In patient #3 immunotherapy reduced the major tumor in the breast and its adherence to the chest wall. Hence, surgical excision of the tumor was carried out uneventfully and there has been no evidence of local recurrence of tumor 6 months after surgery. Patient #4 underwent chemotherapy with adriamycin, cyclophosphamide and 5 fluorouricil and over a 2 month period has realized a further regression of measurable lesions (91%) and complete healing of ulcerated areas of neoplasm on the chest wall. Since concluding immunotherapy, patient #5 underwent chemotherapy for 6 months during which time her chest wall tumor showed further reduction in size and it was subsequently removed surgically. In addition to her breast cancer, patient #1 had Laennec's cirrhosis, diabetes mellitus and thrombocytopenia at the time of initiation of immunotherapy. She developed a staphylococca bacteremia thought to have arisen from an intravenous catheter site which was brought under control with served in dogs with spontaneous breast cancer after extracorporeal perfusion over SAC may be due in part to the activation of tumor specific antibodies (TSA) in plasma after perfusion. Terman et al, supra. In separate in vitro studies, TSA have been shown to work synergistically with cytosine arabinoside (Ara-C) to inhibit tumor cell replication. Shearer, W. T., Philpott, G. W., and Parker, C. W., Science 182, 1357 (1973); Shearer, W. T., and Mettes, H. J., J. Immunol. 123, 2763 (1979). One aspect of the present invention is a new methodology which augments the magnitude of the tumoricidal response induced by extracorporeal perfusion over immobilized protein A.

Dogs with spontaneous breast adenocarcinoma were given Ara-C, 10 mg/kg, intravenously for 4 hours and showed no significant morphologic changes in their tumor. Seven to 12 days later, the same dogs underwent extracorporeal perfusion over PACC alone, which resulted in hypermic response at single and multiple visible areas of tumor occurring 4 to 8 hours after perfusion and progressing to necrosis of visible tumorous sites by 12 hours. Ten to 21 days later when inflammatory reactions had subsided and tumors had regrown to near original dimensions, each dog underwent a similar extracorporeal perfusion over protein A which was followed by infusion of Ara-C (10mg/kg) for 4 hours in the immediate postperfusion period. This resulted in a more rapid and extensive necrosis of visible tumorous sites than was observed with protein A perfusion alone. Severe hyperemic reactions were evident within 30 minutes to 2 hours after perfusion progressing to necrosis by 12 hours. Normal mammary glands in the same dogs showed no morphologic changes in the course of these tumoricidal reactions. Twelve to 21 days later when tumors had regrown to near original size, all dogs underwent extracorporeal perfusion over a collodion charcoal column with no protein A immobilized and no tumoricidal responses were observed. Three additional dogs underwent only PACC+Ara-C treatment and showed rapid necrotizing reactions. Microscopic examination of the tumor tissue obtained before and 24 hours after treatment with each of these programs where a more extensive necrotizing tumoricidal reaction after the PACC+Ara-C program compared to the PACC regimen alone.

Tumor necrosis as judged by densitometric evaluation of tumor reactions resulting from extracorporeal perfusion over PACC was markedly augmented by administration of a single nontoxic dose of Ara-C in the post-perfusion period. Ara-C infusion exerted no evident tumoricidal response. However, when the drug was given after PACC perfusion, the observed response exceeded that noted after PACC alone. The responses for the PACC+Ara-C regimen was greater than the albebraic sum of responses to Ara-C and PACC suggesting that the effect of the drug was potentiated by PACC perfusion.

EXAMPLE VII

In addition to Ara-C, adriamycin, methotrexate, cyclophosphamide, 5-fluorouricil can be used as the anticancer drug infusion, or combinations thereof for various periods before, during and after perfusion over immobilized protein A with good results. In 2 human patients, the use of adriamycin, 5-fluorouricil and cyclophosphamide resulted in additional tumor killing when given at the conclusion of plasma perfusion treatments.

EXAMPLE VIII

Figure 2:
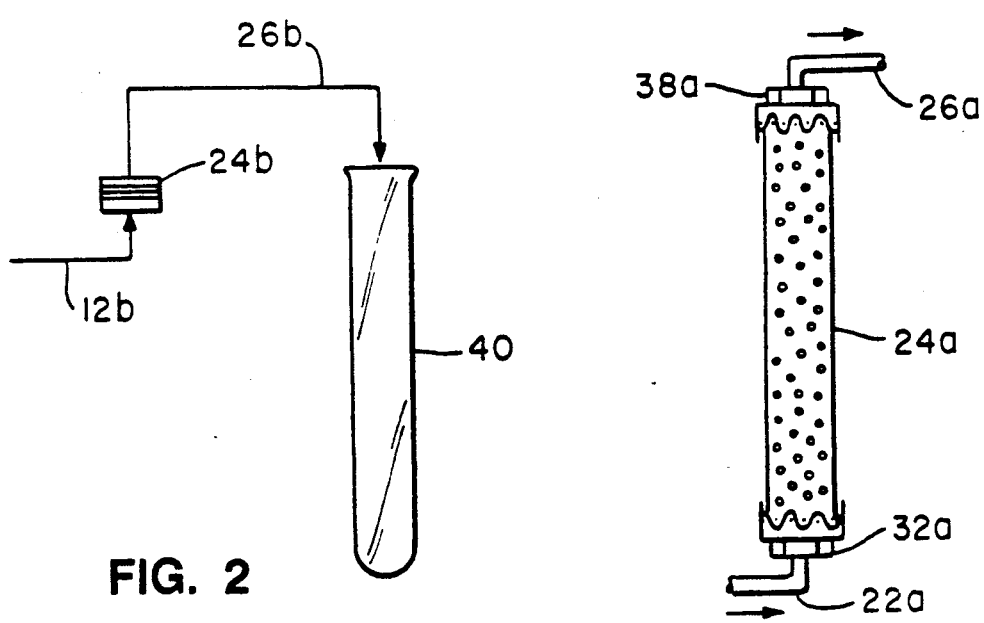
FIG. 2 is a fragmentary schematic view illustrating a miniaturized therapeutic, extracorporeal immunoadsorbent by which small amounts of serum are processed.

Referring now to FIG. 2, a miniaturized protein A collodion charcoal assembly or cartridge 24 is illustrated which enables the processing of small amounts of serum through it.

The miniaturized frisbee 24b is in all particulars the same as the frisbee or cartridge 24 except that it is in miniature form. In practice a preferred size for the perfusion "frisbee" about 12 cm in diameter, with the miniaturized frisbee being about 3 cm in diameter.

Similarly, the miniaturized column 24a is 2 cm tall and 3 cm in diameter; whereas, the perfusion column 24a is 8 cm tall and 3 cm in diameter. The column is useful in testing but not for use in vivo.

In use, a small amount of serum, about 5 ml, enters the miniaturized protein A collodion charcoal immunoadsorbent cartridge 24b in the line 12b and passes through it and out the line 26b and is gathered in a test tube or other suitable container 40.

EXAMPLE IX

In this example, plasma was collected from tumor bearing patients and perfused as described above over protein A immobilized in membranes of collodion. The plasma was stored in protein A perfused plasma banks or perfused directly into other patients with the same cancer at the same or a later time.

Hence, plasma from tumor bearing patients may be processed over immobilized protein A in two ways: (a) by direct extraction from the patient, cell separation and plasma perfusion over immobilized protein A in an extracorporeal continuous flow system and method; and (b) by separate plasma removal from a tumor bearing patient followed by perfusion off-line over immobilized protein A at a later time.

The various aspects of the present invention are therefor well suited and adapted to attain the objects and ends and have the advantages and features mentioned as well as those which are inherent therein.

While presently preferred embodiments of the various aspects of the invention have been given for the purposes of disclosure, changes can be made therein which are covered by the claims and the equivalents.

What is claimed is:

1. A therapeutic immunoadsorbent effective in treatment of cancer comprising SPA non-covalently immobilized in membranes of collodion on an inert carrier.

2. The immunoadsorbent of claim 1 where,
   the SPA is immobilized closely adjacent to surfaces of particles of activated charcoal.

3. The immunoadsorbent of claim 1 where,
   the carrier is particles of activated coconut charcoal, and
   the SPA is immobilized closely adjacent to surfaces of the particles of activated coconut charcoal.

4. A therapeutic immunoadsorbent cartridge effective in treatment of cancer comprising,
   a container, SPA non-covalently immobilized on an inert carrier disposed in the container,
   at least one screen in the container on an outflow side of the container, and
   flow passage means connected to the container arranged for flow into the container, through the immobilized SPA, through the screen and out of the container.

5. The immunoadsorbent cartridge of claim 4 where,
   the SPA is immobilized in membranes of collodion.

6. The immunoadsorbent cartridge of claim 4 where,
   the carrier comprises inert particles, and
   the SPA is immobilized closely adjacent to surfaces of the inert particles.

7. The cartridge of claim 6 where,
   the particles are premoistened, loaded into a fluid bed and physically separated from one another.

8. The immunoadsorbent cartridge of claim 4 where,
   the carrier comprises particles of activated coconut charcoal, and
   the SPA is immobilized closely adjacent to surfaces of the particles of activated charcoal.

9. The cartridge of claim 8 where,
   the particles are physically separated from one another.

10. A method of perfusion useful in treatment of cancer comprising,
    perfusing plasma over SPA non-covalently immobilized in membranes of collodion.

11. The method of perfusion of claim 10 where, the perfusion is over the SPA non-covalently immobilized closely adjacent to surfaces of particles of activated charcoal.

12. The method of perfusion of claim 10 where, the perfusion is over SPA non-covalently immobilized closely adjacent to inert support particles.

13. The method of perfusion of claim 10 where, the perfusion is over the SPA immobilized closely adjacent to surfaces of particles of activated coconut charcoal.

14. The method of claim 10 where for adults,
the quantity of SPA ranges from about 0.12 to about 5.0 mg,
the volume of plasma perfused over the SPA ranges from about 5 to about 300 ml, and
the flow rate of the plasma ranges from about 2 to about 5 ml/min.

15. The method of claim 10 where for children,
the quantity of SPA ranges from about 0.001 to mg to 0.01 mg,
the volume of plasma perfused over the SPA ranges from about 5 to about 50 ml, and
the flow rate of the plasma ranges from about 2 to about 5 ml/min.

16. The method of claim 10 where,
the quantity of SPA ranges from about 0.1 to about 5.0 mg,
the volume of plasma perfused over the SPA ranges from about 5 ml to about 300 ml,
the flow rate of the plasma ranges from about 2 to about 5 ml/min, and
the quantity and volume is adjusted for body weight.

17. A method of extracorporeal perfusion useful in treatment of cancer comprising,
flowing blood from a host,
separating plasma from the blood,
perfusing the plasma over SPA non-covalently immobilized on inert particles,
combining the perfused plasma and the blood from which the plasma has been separated to form recombined whole blood, and
flowing the recombined whole blood back into the host.

18. The method of extracorporeal perfusion of claim 17 where,
the perfusion is over the SPA non-covalently immobilized in membranes of collodion on the inert particles.

19. The method of extracorporeal perfusion of claim 18 where,
the perfusion is over the protein A immobilized closely adjacent to surfaces of particles of activated charcoal.

20. The method of extracorporeal perfusion of claim 17 where,
the quantity of SPA ranges from about 0.1 mg to about 5.0 mg,
the volume of plasma perfused over the SPA ranges from about 5.0 ml to about 300 ml,
the flow rate of the plasma ranges from about 2 to about 5 ml/min, and
the quantity and volume is adjusted for body weight.

21. The method of extracorporeal perfusion of claim 17 where,
the immobilized SPA particles are premoistened, loaded into a fluid bed and separated from one another.

22. The method of claim 17 where, the perfusion is over the SPA convalently bound to and immobilized upon a biocompatible inert carrier.

23. A perfusion system comprising,
a separator operable to separate plasma from whole blood,
a therapeutic non-covalently immobilized protein A immunoadsorbent, a chamber,
an inflow line connected to the separator and adapted to be connected to a host for inflow of blood into the system,
a plasma flow line connected to the separator and to the therapeutic immobilized protein A immunoadsorbent operable to flow plasma from the separator to the immunoadsorbent,
a formed element flow line connected to the separator and to the chamber operable to flow formed elements from the separator into the chamber,
a perfused plasma flow line connected to the therapeutic protein A immunoadsorbent and into the chamber operable to flow perfused plasma from the immunoadsorbent to the chamber to form recombined whole blood with the formed elements,
an outflow line connected to the chamber adapted to be connected to the host operable to flow the recombined whole blood back into the host, and
non-pulsating pump means effective to flow the whole blood, plasma, formed elements and recombined whole blood through the system above thrombogenicity levels.

24. The perfusion system of claim 23 including,
a cartridge including a container,
particles of activated charcoal disposed in the container having the SPA non-covalently immobilized closely adjacent to their surfaces, the particles being separated from one another, and
screens in the container on each side of the particles of activated charcoal arranged so that flow is through one of the screens, across the particles of activated charcoal and through the other of the screens.

25. The perfusion system of claim 24 where,
the therapeutic protein A immobilized immunoadsorbent is in the form of a flat cartridge.

26. The perfusion system of claim 24 where,
the cartridge is in the form of a column.

27. A method of extracorporeal perfusion comprising,
perfusing plasma over protein A non-covalently immobilized in membranes of collodion closely adjacent to support particles, and storing the perfused plasma.

28. The method of claim 27 where,
the support particles are activated charcoal.

29. The method of claim 27 where, the perfusion is over the SPA covalently bound to and immobilized upon a biocompatible inert carrier.

30. A method of treating cancer in a patient comprising,
infusing into the patient plasma perfused over-non-covalently immobilized protein A, and
giving the patient a non-toxic drug infusion.

31. The method of treating cancer of claim 30 where, the drug infusion is given immediately following the infusion of the plasma.

32. The method of claim 31 where, the drug is selected from the group consisting of cytosine arabinoside, adriamycin, 5-fluorouracil, cyclophosphamide and combinations thereof.

33. A therapeutic immunoadsorbent effective in treatment of cancer comprising SPA covalently bound to, and immobilized upon, a biocompatible inert carrier.

34. A therapeutic immunoadsorbent of claim 33 wherein said inert carrier is selected from the group consisting of nylon, methacrylate and polystyrene.

35. A therapeutic immunoadsorbent cartridge effective in treatment of cancer comprising, p1 a container,
SPA covalently bound to, and immobilized upon a biocompatible inert carrier disposed in the container,
at least one screen in the container on an outflow side of the container, and
flow passage means connected to the container arranged for flow through the container, through the immobilized SPA, through the screen and out of the container.

36. The immunoadsorbent cartridge of claim 35 where,
said inert carrier comprises particles, and
the SPA is immobilized closely adjacent to surfaces of the inert particles.

37. The immunoadsorbent cartridge of claim 35 wherein said inert carrier is selected from the group consisting of nylon, methacrylate and polystyrene.

38. A method of perfusion useful in treatment of cancer comprising,
perfusing plasma over SPA covalently bound to, and immobilized upon a biocompatible inert carrier.

39. The method of perfusion of claim 38 where, said inert carrier is selected from the group consisting of nylon, methacrylate and polystyrene.

40. The method of claim 38 where for adults, the quantity of SPA ranges from about 0.12 to about 5.0 mg,
the volume of plasma perfused over the SPA ranges from about 5 to about 300 ml, and
the flow rate of the plasma ranges from about 2 to about 5 ml/min.

41. The method of claim 38 where for children,
the quantity of SPA ranges from about 0.001 mg to 0.01 mg,
the volume of plasma perfused over the SPA ranges from about 5 ml to about 50 ml, and
the flow rate of the plasma ranges from about 2 to about 5 ml/min.

42. The method of claim 38 where,
the quantity of SPA ranges from about 0.1 mg to about 5.0 mg,
the volume of plasma perfused over the SPA ranges from about 5 ml to about 300 ml,
the flow rate of the plasma ranges from about 2 to about 5 ml/min, and
the quantity and volume is adjusted for body weight.

43. A therapeutic immunoadsorbent comprising SPA non-covalently immobilized in membranes of collodion on an inert carrier.

44. A therapeutic immunoadsorbent cartridge comprising,
a container,
SPA non-covalently immobilized on an inert carrier disposed in the container,
at least one screen in the container on an outflow side of the container, and
flow passage means connected to the container arranged for flow into the container, through the immobilized SPA, through the screen and out of the container.

45. A method of perfusion comprising,
perfusing plasma over SPA non-covalently immobilized in membranes of collodion.

46. A method of extracorporeal perfusion comprising,
flowing blood from a host,
separating plasma from the blood,
perfusing the plasma over SPA non-covalently immobilized on inert particles,
combining the perfused plasma and the blood from which the plasma has been separated to form recombined whole blood, and
flowing the recombined whole blood back into the host.

47. A therapeutic immunoadsorbent comprising SPA covalently bound to, and immobilized upon, a biocompatible inert carrier.

48. A therapeutic immunoadsorbent cartridge comprising,
a container, SPA covalently bound to, and immobilized upon a biocompatible inert carrier disposed in the container,
at least one screen in the container on an outflow side of the container, and
flow passage means connected to the container arranged for flow through the container, through the immobilized SPA, through the screen and out of the container.

49. The immunoadsorbent cartridge of claim 48 where,
said inert carrier comprises particles, and
the SPA is immobilized closely adjacent to surfaces of the inert particles.

50. The immunoadsorbent cartridge of claim 48 wherein said inert carrier is selected from the group consisting of nylon, methacrylate and polystyrene.

51. A method of perfusion comprising,
perfusing plasma over SPA covalently bound to, and immobilized upon a biocompatible inert carrier.

52. The method of perfusion of claim 51 where, said inert carrier is selected from the group consisting of nylon, methacrylate and polystyrene.

* * * * *

UNITED STATES PATENT AND TRADEMARK OFFICE
CERTIFICATE OF CORRECTION

PATENT NO. : 5,091,091

DATED : 2/25/92

INVENTOR(S) : David S. Terman

It is certified that error appears in the above-identified patent and that said Letters Patent is hereby corrected as shown below:

Column 1, line 4, after the title and before "CROSS REFERENCE TO RELATED APPLICATION, please insert --The invention described herein was made in the course of or under grants from the United States government.--

Signed and Sealed this

Twelfth Day of April, 1994

Attest:

Attesting Officer

BRUCE LEHMAN

Commissioner of Patents and Trademarks